United States Patent [19]

Conti et al.

[11] Patent Number: 5,425,920
[45] Date of Patent: Jun. 20, 1995

[54] VIAL FOR CHEMICAL REAGENTS

[75] Inventors: Davide Conti, Milan; Rosario Di Lorenzo, Cassina de Pecchi, both of Italy

[73] Assignee: Carlo Erba Reagenti S.r.L., Milan, Italy

[21] Appl. No.: 212,424

[22] Filed: Mar. 14, 1994

[30] Foreign Application Priority Data

Feb. 23, 1994 [IT] Italy .............................. MI94U0121

[51] Int. Cl.$^6$ .............................................. B01L 3/00
[52] U.S. Cl. ..................................... 422/102; 422/100; 422/103; 435/296; 436/180; 436/810
[58] Field of Search ................. 422/102, 99, 100, 101, 422/103; 435/296; 436/180, 810; 215/32, 257, 228; 222/552, 91; 220/267, 277, 360

[56] References Cited

U.S. PATENT DOCUMENTS

| 4,134,511 | 1/1979 | Deussen | 215/32 |
| 4,747,501 | 5/1988 | Greaves | 215/253 |
| 4,964,521 | 10/1990 | Wieland et al. | 215/32 |
| 5,158,213 | 10/1992 | Lataix | 222/189 |
| 5,178,838 | 1/1993 | Sala et al. | 422/102 |
| 5,228,593 | 7/1993 | O'Meara | 222/41 |

Primary Examiner—James C. Housel
Assistant Examiner—Long V. Le
Attorney, Agent, or Firm—Oblon, Spivak, McClelland, Maier, & Neustadt

[57] ABSTRACT

The present invention relates to a vial which can contain metered quantities of a chemical reagent. The vial has its lower or discharge end closed by a breakable diaphragm from which there outwardly extends a flat tang housed and retained in a seat provided within a hollow element. The hollow element is mounted to a hollow body by ribs which enable it to be rotated relative to the hollow body in order to cause the diaphragm to be broken by the tang.

4 Claims, 2 Drawing Sheets

VIAL FOR CHEMICAL REAGENTS

BACKGROUND OF THE INVENTION

1. Field of the Invention

This utility model relates to a vial to contain exactly metered quantities of chemical reagents, in particular high purity chemical reagents of exactly defined concentration, for use in carrying out chemical reactions and/or titrations after predetermined dilution.

2. Discussion of the Related Art

Vials of this type are well known and widely used in chemical and analysis laboratories.

Known vials consist of an elongate hollow body closed at its two ends by breakable membranes. Or, that end of the vial which is to remain at the higher level during the use of the vial (hereinafter known as the upper end), there is usually mounted a furreel provided with a cutting edge to break the membrane adjacent to it, the funnel being used to feed wash water to the vial after the reagent originally contained in it has been discharged (see patents EP-A-0 213 559, EP-A-0 332 914, US-A-4 964 521 and US-A-5 178 838).

In contrast, the closure systems vary greatly for that end of the vial which is to face downwards when the reagent is discharged from it, this being known hereinafter as the lower end of the vial.

EP-A-0 213 559 illustrates a vial the lower end of which is sealedly closed by a membrane identical to that provided at its upper end and also breakable by a cutting edge projecting from a funnel member mounted on the lower end of the vial. With this system the main drawback is that it is very easy to accidentally and dangerously break the membrane which can result in a very dangerous leakage of the reagent from the vial.

EP-A-0332914 and US-A-4964521 illustrate a vial the lower end of which is sealedly closed by a membrane welded to a stronger membrane or part provided at the discharge end of a funnel member mounted on the end of the hollow body to which it is connected by a spiral rib. On rotating the funnel member relative to the hollow body, the closure membrane is torn from the lower end of the vial to allow discharge of the reagent.

This type of vial has two main drawbacks, namely that the membrane of the hollow body has to be properly welded to that of the funnel member, and that a non-negligible quantity of the reagent remains trapped between the lower end of the hollow body and the funnel member mounted on it.

In addition, none of the aforesaid vials can be reclosed (at their lower end) after being opened.

US-A-5178838 comprises, at the lower end of the vial described in it, a device of a tap type comprising two mutually cooperating conical surfaces, which can be pressed one against the other close the vial or withdrawn one from the other to enable the reagent contained in it to be discharged. This type of tap device has the merit of enabling the flow of reagent from the vial to be interrupted at any moment, but has the drawback of being relatively costly, of suffering from undesirable and dangerous leakage (especially during transportation of the vial), and of retaining portions of the reagent which drip to the outside after the tap device has been closed.

SUMMARY OF THE INVENTION

A main object of the present invention is to provide a vial for chemical reagents which is of simple and economical construction, ensures hermetic sealing of the vial before its use, and cannot be opened involuntarily or accidentally.

Preferably, the vial is to be constructed in such a manner as to be easily reclosed at its lower end after delivery of part of the reagent originally contained in the vial.

These and further objects are attained by a vial comprising an elongate hollow body which is sealed hermetically at one end by a membrane breakable by the action of a cutting edge projecting from a funnel member which can be superposed and forced onto said end, and is closed at its other end by an element breakable by a movable part on this latter end, characterized in that said element comprises a flat tang rigid with and projecting outwards from a breakable diaphragm which seals said other end of the hollow body, said movable part comprising a hollow element open at both ends and connected to the hollow body by ribs which enable it to rotate axially relative to the hollow body, within said hollow element there being provided at least one seat for housing and retaining said tang.

Preferably said flat tang is rigid with the major base of a frusto-conical appendix, the minor base of which is rigid with said diaphragm, said connection ribs between said element and the hollow body being in the form of spiral ribs.

BRIEF DESCRIPTION OF THE DRAWINGS

The structure and characteristics of the vial will be more apparent from the description of a preferred embodiment thereof given with reference to the accompanying drawings, in which.

DESCRIPTION OF PREFERRED EMBODIMENT

Figure 1:
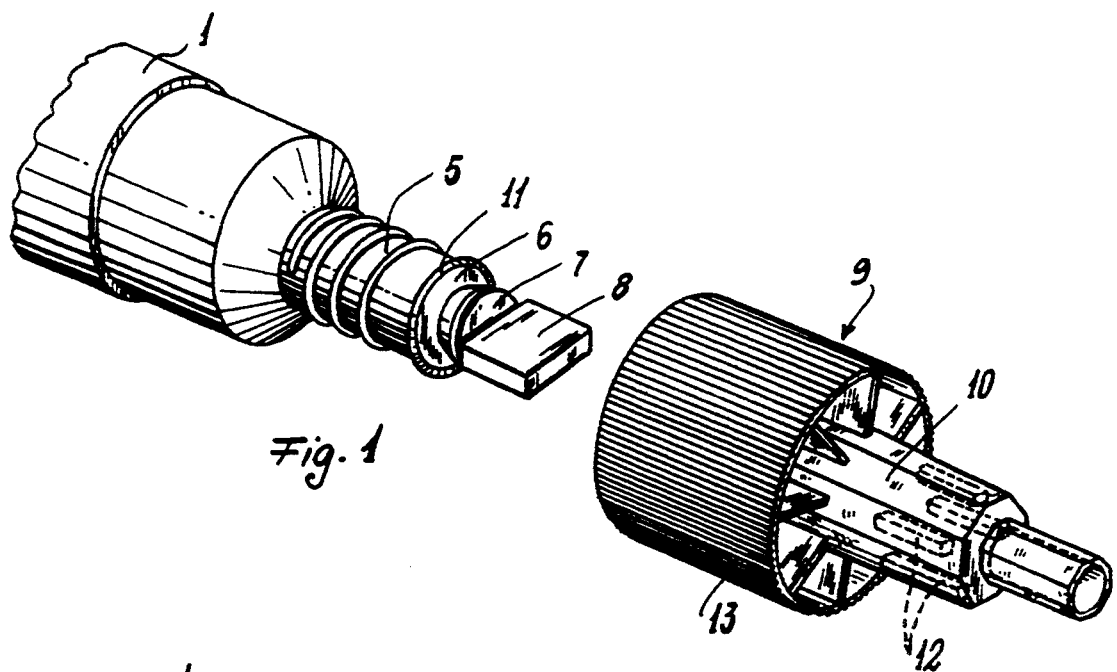
FIG. 1 is a perspective view of that which is to be considered as the lower end of the vial, shown still sealed and with the two component parts which cooperate with each other being shown spaced apart.
Figure 5:
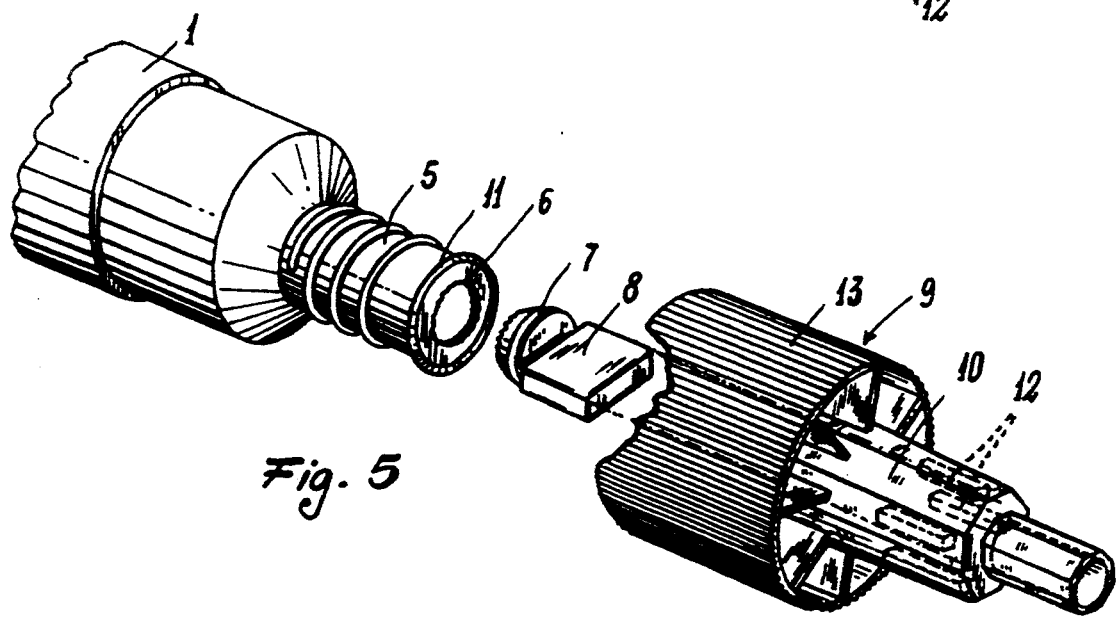
FIG. 5 is an exploded perspective view of the lower end of the vial after its opening.

The vial shown in the drawings comprises an elongate hollow body 1 sealed hermetically at its upper end (with respect to FIG. 2 which shows the vial in the position which it assumes on use) by a breakable membrane 2.

On the upper end of the vial there is mounted a funnel member 3 which is connected to the vial by a screw connection which enables the member 3 to rotate about and move axially along the body 1. A cutting edge 4 is rigid with the funnel member, to cut the membrane 2 on the hollow body 1. From the lower end (with respect to FIGS. 2 and 3) of the body 1 there extends a hollow appendix 5 which is hermetically sealed by a breakable diaphragm 6 with which there is rigid the minor base of a frusto-conical appendix 7, from the major base of which a flat tang 8 projects outwards. When hermetically sealed at its two ends by the membrane 2 and diaphragm 6, the hollow body 1 is enclosed in a perfectly sealed manner arid protects a metered quantity of a chemical reagent.

On the lower end of the hollow body 1 there is mounted a movable part 9 comprising a hollow element 10 open at both ends and connected to the body 1 by spiral ribs (for simplicity not numbered on the drawings) projecting outwards from the appendix 5 and inwards from the hollow element 10 respectively.

From the finites it can be seen that from the free end of the appendix 5 there projects an annular rib 11 which interferes (FIG. 3) with an annular rib or groove provided in the hollow element 10 to prevent a withdrawing from the appendix 5 when the vial is opened.

Figure 2:
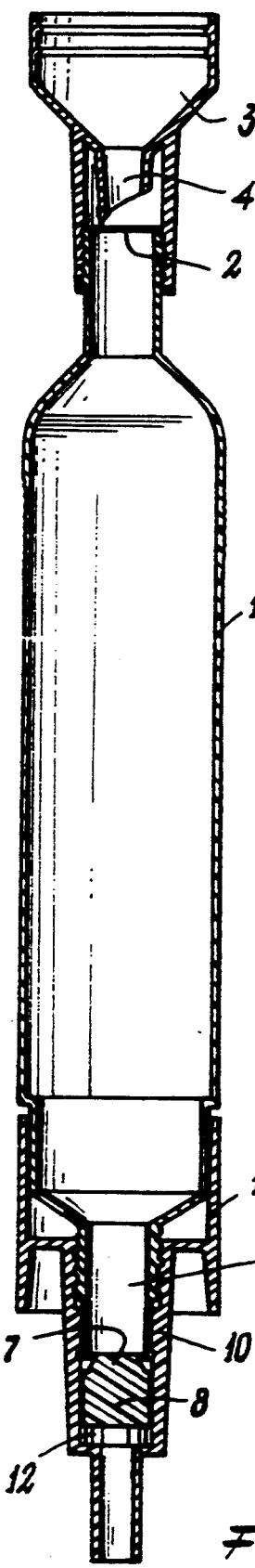
FIG. 2 is a longitudinal section through the sealed vial before its opening.
Figure 3:
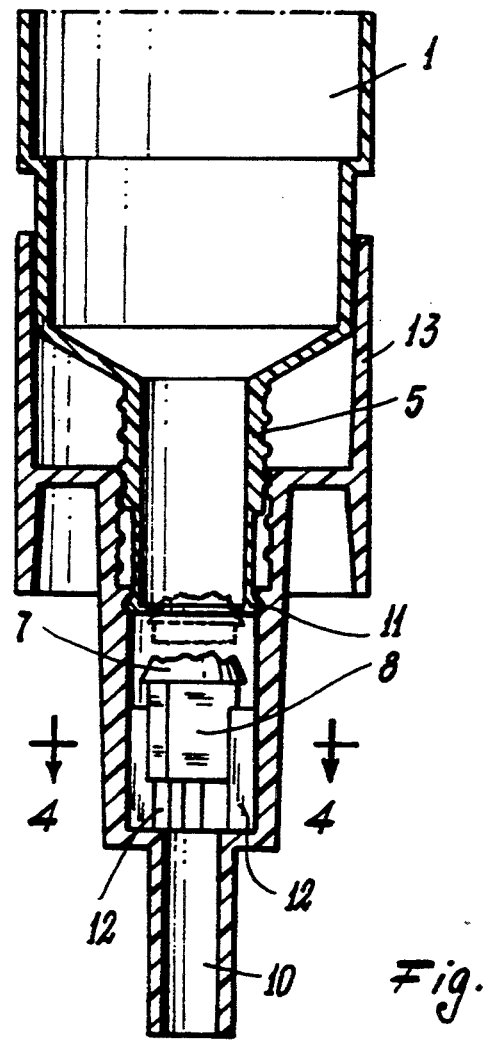
FIG. 3 shows to an enlarged scale the lower end of the vial after its opening.
Figure 4:
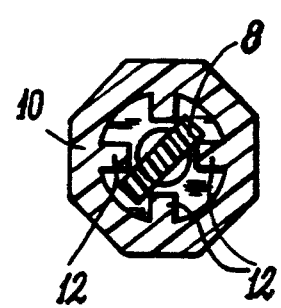
FIG. 4 is a cross-section through the vial on the line 4—4 of FIG. 3.

Inwards from the hollow element 10 there project longitudinal teeth 12 defining between them longitudinal seats which house the tang 8 when the movable part 9 is pushed (without undergoing rotation) onto the respective lower end of the body 1 during the assembly of the vial. Given the elasticity of the plastics material with which the vial is constructed, the ribs of the hollow element 10 can easily pass over the annular rib 11 and spiral ribs of the hollow appendix 5, to enable the tang 8 to easily penetrate into one of the seats defined by the teeth 12. At this point the vial is complete and ready for use (FIG. 2). When all or part of the reagent contained in the body 1 is to be used, the membrane 2 is broken by acting on the funnel member 3, after which the hollow element 10 is rotated (by gripping with one hand a tubular wall 13 projecting from the element and extending towards the adjacent outer surface of the body 1) relative to the body 1, to hence subject the tang 8 to torsion with consequent breakage of the diaphragm 6 (as shown in FIG. 3 and in the exploded view of FIG. 2), with consequent emergence of the reagent through the free end of the hollow element 10. To vary the outflow of reagent from the body 1, the part 9 is screwed onto the appendix 5 to raise (with respect to FIGS. 2 and 3) the tang 8 and with it the frusto-conical appendix 7 to cause said appendix to penetrate into the hole in the diaphragm 6 (as shown by dashed lines in FIG. 3).

It can be seen that in no case does the presence of the appendix 7 and tang 8 within the hollow element 10 appreciably hinder the outflow of the chemical reagent when the vial has been opened.

We claim:

1. A vial for chemical reagents, the vial comprising:
    an elongate hollow body having a first end which is hermetically sealed by a membrane, said membrane being breakable by a cutting edge of a funnel which is adapted to be mounted on said first end of said elongate hollow body;
    a closing element for closing a second end of said elongate hollow body, said closing element comprising a breakable diaphragm which closes said second end of the elongate hollow body and a flat tang which is rigid with and outwardly projects from said breakable diaphragm; and
    a movable part threadedly mounted on said second end of said elongate hollow body so as to be axially movable with respect to said elongate hollow body, said movable part comprising a hollow element which is open at both ends, an interior surface of said hollow element comprising a plurality of longitudinal teeth such that spaces are defined between said longitudinal teeth, said flat tang being insertable into said spaces defined between said longitudinal teeth, wherein a movement of said movable part away from said second end of said elongate body causes said flat tang which is inserted between said spaces defined between said longitudinal teeth and which is rigid with said diaphragm to move with said movable part and thereby break said diaphragm.

2. A vial as claimed in claim 1, further comprising a frusto-conical appendix defined between said flat tang and said diaphragm, said frusto-conical appendix having a major base which is rigid with said flat tang, and a minor base which is rigid with said diaphragm.

3. A vial as claimed in claim 1, further including connection ribs formed on said second end of said hollow element, said connection ribs are in the form of spiral ribs.

4. A vial as claimed in claim 3, wherein a tubular wall projects from said hollow element, said tubular wall extending towards an adjacent outer surface of the elongate hollow body.

* * * * *